(12) United States Patent
Andaluz

(10) Patent No.: US 11,559,478 B1
(45) Date of Patent: Jan. 24, 2023

(54) CLEANSING CREAM FORMULATION

(71) Applicant: Ann-Marie Babi Andaluz, Sunrise, FL (US)

(72) Inventor: Ann-Marie Babi Andaluz, Sunrise, FL (US)

(*) Notice: Subject to any disclaimer, the term of this patent is extended or adjusted under 35 U.S.C. 154(b) by 0 days.

(21) Appl. No.: 17/123,274

(22) Filed: Dec. 16, 2020

Related U.S. Application Data

(60) Provisional application No. 62/948,568, filed on Dec. 16, 2019.

(51) Int. Cl.
| | |
|---|---|
| *A61K 8/92* | (2006.01) |
| *A61Q 19/10* | (2006.01) |
| *A61K 8/9794* | (2017.01) |
| *A61K 8/36* | (2006.01) |
| *A61K 8/04* | (2006.01) |

(52) U.S. Cl.
CPC ............... *A61K 8/922* (2013.01); *A61K 8/04* (2013.01); *A61K 8/361* (2013.01); *A61K 8/9794* (2017.08); *A61Q 19/10* (2013.01)

(58) Field of Classification Search
None
See application file for complete search history.

(56) References Cited

U.S. PATENT DOCUMENTS

| | | | |
|---|---|---|---|
| 5,547,985 A | 8/1996 | Brown-Skrobot et al. | |
| 6,479,045 B2 | 11/2002 | Bologna et al. | |
| 9,198,852 B2 | 12/2015 | Burt et al. | |
| 9,622,949 B2 | 4/2017 | Panin | |
| 9,668,948 B2 | 6/2017 | Klingman | |
| 9,913,871 B2 | 3/2018 | Ellington et al. | |
| 9,919,018 B2 | 3/2018 | Ellington et al. | |
| 10,004,761 B2 | 6/2018 | Levy et al. | |
| 10,064,881 B2 | 9/2018 | Siiberstein et al. | |
| 2005/0037033 A1 | 2/2005 | Camus-Bablon et al. | |
| 2006/0115440 A1 | 6/2006 | Arata et al. | |
| 2007/0041924 A1 | 2/2007 | Gupta | |
| 2009/0149361 A1 | 6/2009 | Adkison et al. | |
| 2011/0178488 A1 | 7/2011 | BaLazs | |
| 2017/0007652 A1 | 1/2017 | Quave et al. | |
| 2018/0021503 A1 | 1/2018 | Stewart | |
| 2018/0185268 A1 | 7/2018 | Frushour et al. | |
| 2019/0053993 A1 | 2/2019 | Wilson et al. | |
| 2019/0262292 A1 | 8/2019 | De Szalay et al. | |
| 2019/0275099 A1 | 9/2019 | Tanner | |

*Primary Examiner* — David J Blanchard
*Assistant Examiner* — Sarah J Chickos
(74) *Attorney, Agent, or Firm* — The Patent Professor, P.A.; John Rizvi

(57) ABSTRACT

A chemical-free, body cleansing cream formulation is provided comprising organic *Aloe vera* gel, coconut oil, sunflower oil, shea butter, witch hazel, one or more essential oils such as clary sage or distilled lime, and one or more pH-balancing agents such as apple cider vinegar or citric acid. The formulation is a natural alternative to soap which does not include chemicals such as sodium hydroxide. The cleansing cream has no soapsuds and produces no foam, and yet can still cleanse the most intimate areas of the body with very little to no risk of skin irritation. Alternatively, the cream or formulation can include *Tribulus*, witch hazel, horny goat weed (*Epimedium*), shea butter, *ginseng*, citric acid, coconut oil, almond oil, and flaxseed.

20 Claims, No Drawings

CLEANSING CREAM FORMULATION

CROSS-REFERENCE TO RELATED APPLICATIONS

This application claims the benefit of U.S. Provisional Patent Application Ser. No. 62/948,568 filed on Dec. 16, 2019, which is incorporated by reference herein in its entirety.

FIELD OF THE INVENTION

The present invention relates generally to a cleansing cream, and more particularly, to a chemical-free cleansing cream formulation designed for washing the intimate areas of a female or male body.

BACKGROUND OF THE INVENTION

A surfactant is a solid chemical compound that dissolves in a liquid such as water. The resulting solution has a lower surface tension than the liquid alone. Soap is an example of a surfactant that dissolves in water and produces a solution with a lower surface tension than the water alone. In case the solution is brought in contact with oil or dirt, the soap in the solution lowers the surface tension between the water and the oil, or between the water and the dirt. In this way the solution made of water and soap can be used to wash away oil and dirt. In general, a solution of a surfactant in a liquid is referred to as a detergent.

Sodium hydroxide (NaOH) is a solid base which can be used as a surfactant. Sodium hydroxide is soluble in water and therefore, used for producing soaps and detergents. The production of soap with sodium hydroxide is made by saponification, which is the conversion of fat or oil into soap and alcohol by the action of heat in the presence of Sodium hydroxide.

Typically, soap contains a high amount of synthetic ingredients, which do not contribute to the cleansing of the skin and may in fact adversely interact with the skin. Therefore, the cleansing with soap everyday can cause topical skin problems like acne and eczema. For this reason, soap substitutes are often used instead of soap. A soap substitute is a detergent or a cleansing cream, other than soap, which can be used for cleaning the skin and may provide other advantages, effects or benefits compared to soap. A well-known example of a soap substitute is shower gel.

Shower gels are liquids for cleaning the body during showers. A shower gel uses synthetic detergents to clean the skin. However, the surfactants of shower gels do not come from saponification. Instead, shower gels use synthetic detergents for surfactants derived from either plant-based sources or petroleum. Therefore, shower gels have a lower pH value compared to soap.

Different shower gels and soaps are also used to clean the vaginal area. However, current vaginal cleansing gels and soaps are typically not hormonally balanced. Furthermore, surfactants and detergents also facilitate foam, as reducing the surface tension of a liquid also reduces the work needed to create foam on the surface of a liquid.

Accordingly, there remains a need in the art for a solution to at least one of the aforementioned problems or for new, improved variations of human body cleansers, such as for the intimate areas of a male or female body. For example, it would be desirable to obtain a natural and chemical-free cleansing cream to clean the vaginal area, which does not foam and is hormonally balanced.

SUMMARY OF THE INVENTION

The present invention is directed to a chemical-free cleansing cream, which is a natural alternative to soap and is particularly useful for cleansing intimate areas of the body. The formulation in accordance with the invention comprises preferably organic *Aloe vera* gel, coconut oil, sunflower oil, unrefined or refined shea butter, witch hazel, at least one essential oil, and at least one pH-balancing agent. The cleansing cream does not include chemicals such as sodium hydroxide, which makes the invention different from soap and a natural alternative to soap. The cleansing cream has no soapsuds and produces no foam, and yet can still cleanse the most intimate areas of the body with very little to no risk of skin irritation, contrary to conventional soaps. Furthermore, in different embodiments of the invention, the cleansing cream may increase the female and/or male user's libido.

In a first implementation of the invention, a cleansing cream formulation which may be particularly, but not only, suitable for a female user and may be advantageously, but not only, applied to intimate areas of the user's body, comprises:
  *Aloe vera* gel,
  coconut oil,
  sunflower oil,
  shea butter,
  witch hazel,
  at least one essential oil, and
  at least one pH-balancing agent.

In a second aspect, the *Aloe vera* gel may be organic.

In another aspect, the coconut oil may be extracted from the kernel or meat of mature coconuts.

In another aspect, the sunflower oil may be refined.

In another aspect, the sunflower oil may be unrefined.

In another aspect, the sunflower oil may be designed as an emollient.

In another aspect, the sunflower oil may comprise polyunsaturated fat, 59% linoleic acid, monounsaturated fat, 30% oleic acid.

In another aspect, the sunflower oil may contain a relatively high amount of vitamin E.

In another aspect, the sunflower oil may be a triglyceride.

In another aspect, the sunflower oil may comprise: 5% saturated palmitic acid, 6% saturated stearic acid, 30% monounsaturated omega-9 oleic acid, and 59% polyunsaturated omega-6 linoleic acid.

In another aspect, the sunflower oil may be plant bred as high-linoleic, high-oleic, mid-oleic, and high-stearic combined with high-oleic, wherein high-linoleic, comprises 69% linoleic acid, high-oleic comprises 82% oleic acid, mid-oleic comprises 65% oleic acid, and high-stearic with high-oleic comprises 18% stearic acid and 72% oleic acid.

In another aspect, the sunflower oil may comprise phytosterols, polyphenols, squalene, and/or terpenoids.

In another aspect, the sunflower oil may be extracted using chemical solvents, e.g., hexane, or expeller pressing, i.e., squeezed directly from sunflower seeds by crushing them under low-temperature without using chemical solvents.

In another aspect, the sunflower oil may be a refined sunflower oil, optionally through solvent extraction, degumming, neutralization, and bleaching to make the sunflower oil more stable.

In another aspect, the sunflower oil may be an unrefined sunflower oil to make the sunflower oil less heat-stable.

In another aspect, the shea butter may be refined.

In another aspect, the shea butter may be unrefined.

In another aspect, the shea butter includes both refined shea butter and unrefined shea butter.

In another aspect, the shea butter may be extracted from the nut of the African shea tree.

In another aspect, the shea butter may be designed as a moisturizer, salve or lotion.

In another aspect, the shea butter may be designed as shea butter extract.

In another aspect, the shea butter may be designed as a complex fat.

In another aspect, when the shea butter may be added to a non-saponifiable material the mixture comprises the following fatty acids: 40-60% oleic acid, 20-50% stearic acid, 3-11% linoleic acid, 2-9% palmitic acid, less than 1% linolenic acid and less than 1% arachidic acid.

In another aspect, the melting point of the shea butter may be at body temperature.

In another aspect, the shea butter may be designed as raw or unrefined shea butter, optionally extracted using water, refined shea butter, highly refined shea butter extracted with solvents such as hexane, uncontaminated shea butter, and shea butter with contaminants.

In another aspect, the witch-hazel may be designed as an extract of witch-hazel to prevent psoriasis, eczema and dehydration of skin, and ease discomfort involving vaginal soreness.

In another aspect, the witch-hazel may be extracted from the leaves and bark of the North American witch-hazel to produce an astringent decoction as a cooling agent for the skincare.

In another aspect, the witch-hazel may be designed as witch-hazel water or a semisolid ointment, cream, gel, or salve.

In another aspect, the witch-hazel may be designed as a topical agent.

In another aspect, the witch-hazel may comprise calcium oxalate, gallotannins, safrole, and essential oil chemicals such as carvacrol and eugenol.

In another aspect, the at least one essential oil may comprise one or more of clary sage, distilled lime, tea tree oil or lavender.

In another aspect, the at least one pH-balancing agent may include at least one of apple cider vinegar and citric acid, and preferably both.

In another aspect, the apple cider vinegar may be made from fermented apple juice.

In another aspect, the citric acid may be a citrate, trisodium citrate or triethyl citrate.

In a second implementation of the invention, a cleansing cream formulation, which may be particularly, but not only, suitable for a male user, and may be advantageously, but not only, applied to intimate areas of the user's body, comprises:

Tribulus,
witch hazel,
horny goat weed (*Epimedium*),
shea butter,
*ginseng*, citric acid,
coconut oil,
almond oil, and
flaxseed.

These and other objects, features, and advantages of the present invention will become more readily apparent from the detailed description of the preferred embodiments, which follows.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is directed to a chemical-free cleansing cream or formulation, which is a natural alternative to soap. The formulation is particularly useful for cleansing intimate areas of the body; however, alternative uses are also contemplated without departing from the scope of the present disclosure.

In a first embodiment of the invention, the cleansing cream comprises *Aloe vera* gel, coconut oil, sunflower oil, shea butter, witch hazel, at least one essential oil, and at least one pH-balancing agent. Such embodiment may be particularly suitable for a female user, and may be advantageously, but not only, applied to intimate areas of the user's body.

The *Aloe vera* gel provides the formulation with a relatively thick consistency, and with beneficial properties such as healing, soothing, and antibacterial, for instance and without limitation. In some embodiments, the *Aloe vera* gel may be 40% *Aloe vera* gel. In preferred embodiments, the *Aloe vera* gel may be organic, i.e. produced or involving production without the use of chemical fertilizers, pesticides, or other artificial agents. For instance, preferred embodiments of the formulation include 40% organic *Aloe vera* gel.

The coconut oil, in turn, may be extracted from the kernel or meat of mature coconuts. The coconut oil contains a relatively high amount of saturated fat, and is relatively slow to oxidize. This makes the coconut oil resistant to rancidification and typically capable of lasting up to six months at 24° C. (75° F.) without spoiling.

The sunflower oil comprised in the formulation provides vitamin E to the formulation. The sunflower oil is designed as an emollient, and may comprise polyunsaturated fat, 59% linoleic acid, monounsaturated fat, 30% oleic acid, and contain a relatively high amount of vitamin E. The sunflower oil can also be designed as a triglyceride and comprise 5% saturated palmitic acid, 6% saturated stearic acid, 30% monounsaturated omega-9 oleic acid, 59% polyunsaturated omega-6 linoleic acid. The sunflower oil may be plant bred as high-linoleic, high-oleic, mid-oleic, and high-stearic combined with high-oleic, wherein high-linoleic, comprises 69% linoleic acid, high-oleic comprises 82% oleic acid, mid-oleic comprises 65% oleic acid, and high-stearic with high-oleic comprises 18% stearic acid and 72% oleic acid. The sunflower oil may also comprise phytosterols, polyphenols, squalene, and/or terpenoids.

Furthermore, the sunflower oil is pressed from the seeds of the sunflower and may be extracted using chemical solvents, e.g., hexane, or expeller pressing, i.e., squeezed directly from sunflower seeds by crushing them under low-temperature without using chemical solvents. The sunflower oil used in the formulation of the present disclosure may be a refined sunflower oil, optionally through solvent extraction, de-gumming, neutralization, and bleaching, to make the sunflower oil more stable. The sunflower oil is can also be an unrefined sunflower oil to make the sunflower oil less heat-stable.

The shea butter, which may also be unrefined or refined, contributes to provide a cream effect or creamy texture to the formulation. In some embodiments, the shea butter includes both refined shea butter and unrefined shea butter. Alternative embodiments are contemplated, however, in which the shea butter may be either refined or unrefined.

The shea butter is extracted from the nut of the African shea tree and may be designed as a moisturizer, salve or lotion. The shea butter can also be designed as shea butter extract and/or a complex fat. When the shea butter is added to a non-saponifiable material, the mixture may comprise the following fatty acids: 40-60% oleic acid, 20-50% stearic acid, 3-11% linoleic acid, 2-9% palmitic acid, less than 1% linolenic acid and less than 1% arachidic acid.

The melting point of the shea butter is at body temperature and the shea butter absorbs relatively rapid into the skin, acts as a refatting agent, and binds relatively good in water to make it suitable for skin care. The shea butter is designed as raw or unrefined shea butter, optionally extracted using water, refined shea butter, highly refined shea butter extracted with solvents such as hexane, uncontaminated shea butter, and shea butter with contaminants.

The witch hazel, in turn, is provided as an astringent. The witch-hazel is designed as an extract of witch-hazel and is often used to prevent psoriasis, eczema and dehydration of skin, and ease discomfort involving vaginal soreness, and is extracted from the leaves and bark of the North American witch-hazel to produce an astringent decoction as a cooling agent for the skincare. The witch-hazel may be designed as witch-hazel water or a semisolid ointment, cream, gel, or salve and acts as a topical agent, and comprises calcium oxalate, gallotannins, safrole, and essential oil chemicals such as carvacrol and eugenol.

The at least one essential oil may include one or more of clary sage (which may provide a natural hormonal balancing effect and/or—pH balancing), distilled lime, tea tree oil or lavender, for instance and without limitation.

The at least one pH-balancing agent balances the pH value of the formulation, and may include apple cider vinegar and/or citric acid, for instance and without limitation. In some preferred embodiments, the formulation as per the invention may include both apple cider vinegar and citric acid. The apple cider vinegar is made from fermented apple juice. The citric acid is a citrate, trisodium citrate or triethyl citrate.

The formulation of the present invention may further include at least one scent or odorous agent.

The cleansing cream can be produced by batch production.

In a first example of the first embodiment of the cleansing cream formulation of the present disclosure, the formulation comprises the following components:

| Amount | Component |
| --- | --- |
| 0.5 cup (120 ml) | Organic aloe vera gel |
| 2 tbsp (30 ml) | Coconut oil |
| 0.5 cup (120 ml) | Sunflower oil |
| 0.5 cup (120 ml) | Shea butter |
| 2 tbsp (30 ml) | Alcohol-free witch hazel |
| 0.2 oz (6 grams) | Clary sage and distilled lime essential oil |
| 1 tbsp (15 ml) | Apple cider vinegar |
| 0.5 tbsp (7.4 ml) | Citric acid |

In a second example of the first embodiment of the cleansing cream formulation of the present disclosure, the formulation comprises the following components:

| Amount | Component |
| --- | --- |
| 4 cups (960 ml) | Organic aloe vera gel |
| 2 tbsp (30 ml) | Coconut oil |
| 1 cup (240 ml) | Sunflower oil |
| 5 tbsp (75 ml) | Shea butter |
| 0.5 cup (120 ml) | Alcohol-free witch hazel |
| 0.2 oz (6 grams) | Clary sage and distilled lime essential oil |
| 3 tbsp (45 ml) | Apple cider vinegar |
| 2 tbsp (30 ml) | Citric acid |

In a third example of the first embodiment of the cleansing cream formulation of the present disclosure, the formulation comprises the following components:

| Amount | Component |
| --- | --- |
| 64 fl. oz. (1893 ml) | Organic aloe vera gel |
| 2 cups (480 ml) | Coconut oil |
| 2.5 cups (600 ml) | Sunflower oil |
| 8.7 oz. (247 grams) | Refined shea butter |
| 0.5 pound (227 grams) | Unrefined African shea butter |
| 1 cup (240 ml ) | Alcohol-free witch hazel |
| 0.5 oz (14 grams) | Clary sage |
| 0.5 oz. (14 grams) | Distilled lime |
| 2/8 cup (60 ml) | Unfiltered apple cider vinegar |
| 1/8 cup (30 ml) | Citric acid |

In a second embodiment of the invention, the cleansing cream includes *Tribulus*, witch hazel, horny goat weed (*Epimedium*), shea butter, *ginseng*, citric acid, coconut oil, almond oil, and flaxseed. Such embodiment may be particularly suitable for a male user, and may be advantageously, but not only, applied to intimate areas of the user's body. Almond oil provides vitamin E and a creamy effect to the formulation.

In summary, the invention provides a cleansing cream which is a chemical-free, natural alternative to soap. Unlike soap, the invention does not include chemicals such as sodium hydroxide. The cleansing cream has no soapsuds and produces no foam, and yet can still cleanse the most intimate areas of the body with very little to no risk of skin irritation, contrary to conventional soaps. Furthermore, the cleansing cream in accordance with different embodiments of the invention may contribute to tighten and properly moisture the vaginal area, and increase the female and/or male user's libido.

Since many modifications, variations, and changes in detail can be made to the described preferred embodiments of the invention, it is intended that all matters in the foregoing description be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A cleansing cream formulation for cleansing intimate areas of a person's body, said formulation comprising:
   an amount of organic *Aloe vera* gel of about 120 milliliters, wherein organic *Aloe vera* is defined as *Aloe vera* which is grown without the use of chemical fertilizers, pesticides, or any artificial agents;
   an amount of coconut oil of about 30 milliliters;
   an amount of sunflower oil of about 120 milliliters;
   an amount of shea butter of about 120 milliliters;
   an amount of alcohol-free witch hazel of about 30 milliliters;
   an amount of an essential oil of about 6 grams; and
   an amount of a pH balancing agent of about 20 milliliters to about 25 milliliters.

2. The cleansing cream formulation of claim 1, wherein said sunflower oil is refined.

3. The cleansing cream formulation of claim 1, wherein said sunflower oil comprises about 59 percent linoleic acid by volume and about 30 percent oleic acid by volume.

4. The cleansing cream formulation of claim 1, wherein said sunflower oil comprises about 5 percent saturated palmitic acid by volume, about 6 percent saturated stearic acid by volume, about 30 percent monounsaturated omega-9 oleic acid by volume, and about 59 percent polyunsaturated omega-6 linoleic acid by volume.

5. The cleansing cream formulation of claim 1, wherein said sunflower oil comprises one or more of a phytosterol, a polyphenol, a squalene, and a terpenoid.

6. The cleansing cream formulation of claim 1, wherein said shea butter is refined.

7. The cleansing cream formulation as recited in claim 1, wherein said shea butter comprises about 40 percent to about 60 percent oleic acid by volume, about 20 percent to about 50 percent stearic acid by volume, about 3 percent to about 11 percent linoleic acid by volume, about 2 percent to about 9 percent palmitic acid by volume, less than about 1 percent linolenic acid by volume, and less than about 1 percent arachidic acid by volume.

8. The cleansing cream formulation of claim 1, wherein said essential oil comprises one or more of clary sage essential oil, distilled lime essential oil, tea tree essential oil or lavender essential oil.

9. The cleansing cream formulation of claim 1, wherein said pH balancing agent comprises one or more of apple cider vinegar or citric acid.

10. A cleansing cream formulation for cleansing intimate areas of a person's body, said formulation comprising:
    an amount of organic *Aloe vera* gel of about 960 milliliters, wherein organic *Aloe vera* is defined as *Aloe vera* which is grown without the use of chemical fertilizers, pesticides, or any artificial agents;
    an amount of coconut oil of about 30 milliliters;
    an amount of sunflower oil of about 240 milliliters;
    an amount of shea butter of about 75 milliliters;
    an amount of alcohol-free witch hazel of about 120 milliliters;
    an amount of clary sage essential oil and distilled lime essential oil of about 6 grams;
    an amount of apple cider vinegar of about 45 milliliters; and
    an amount of citric acid of about 30 milliliters.

11. The cleansing cream formulation of claim 10, wherein said sunflower oil is refined.

12. The cleansing cream formulation of claim 10, wherein said sunflower oil comprises about 59 percent linoleic acid by volume and about 30 percent oleic acid by volume.

13. The cleansing cream formulation of claim 10, wherein said sunflower oil comprises about 5 percent saturated palmitic acid by volume, about 6 percent saturated stearic acid by volume, about 30 percent monounsaturated omega-9 oleic acid by volume, and about 59 percent polyunsaturated omega-6 linoleic acid by volume.

14. The cleansing cream formulation of claim 10, wherein said sunflower oil comprises one or more of a phytosterol, a polyphenol, a squalene, and a terpenoid.

15. The cleansing cream formulation of claim 10, wherein said shea butter is refined.

16. The cleansing cream formulation as recited in claim 10, wherein said shea butter comprises about 40 percent to about 60 percent oleic acid by volume, about 20 percent to about 50 percent stearic acid by volume, about 3 percent to about 11 percent linoleic acid by volume, about 2 percent to about 9 percent palmitic acid by volume, less than about 1 percent linolenic acid by volume, and less than about 1 percent arachidic acid by volume.

17. The cleansing cream formulation as recited in claim 10, wherein said alcohol-free witch hazel comprises one or more of calcium oxylate, a gallotannin, and safrole.

18. The cleansing cream formulation as recited in claim 10 wherein said alcohol-free witch hazel comprises one or more of carvacrol and eugenol.

19. The cleansing cream formulation as recited in claim 10, wherein said citric acid comprises one or more of citrate, trisodium citrate, and triethyl citrate.

20. A cleansing cream formulation for cleansing intimate areas of a person's body, said formulation comprising:
    an amount of organic *Aloe vera* gel of about 1900 milliliters, wherein organic *Aloe vera* is defined as *Aloe vera* which is grown without the use of chemical fertilizers, pesticides, or any artificial agents;
    an amount of coconut oil of about 500 milliliters;
    an amount of sunflower oil of about 600 milliliters;
    an amount of refined shea butter of about 250 milliliters;
    an amount of unrefined shea butter of about 230 milliliters;
    an amount of alcohol-free witch hazel of about 240 milliliters;
    an amount of clary sage essential oil of about 15 grams;
    an amount of distilled lime essential oil of about 15 grams;
    an amount of unfiltered apple cider vinegar of about 60 milliliters; and
    an amount of citric acid of about 30 milliliters.

* * * * *